(12) United States Patent
Wilson, III

(10) Patent No.: US 10,314,963 B2
(45) Date of Patent: Jun. 11, 2019

(54) MEDICAL RESERVOIR LEVEL SENSOR

(71) Applicant: Mayo Foundation for Medical Education and Research, Rochester, MN (US)

(72) Inventor: Donald S. Wilson, III, Phoenix, AZ (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 109 days.

(21) Appl. No.: 15/581,524

(22) Filed: Apr. 28, 2017

(65) Prior Publication Data

US 2017/0326288 A1 Nov. 16, 2017

Related U.S. Application Data

(60) Provisional application No. 62/336,852, filed on May 16, 2016.

(51) Int. Cl.
*A61M 1/36* (2006.01)
*A61M 1/10* (2006.01)

(52) U.S. Cl.
CPC ........ *A61M 1/3624* (2013.01); *A61M 1/1086* (2013.01); *A61M 1/3627* (2013.01);
(Continued)

(58) Field of Classification Search
CPC ........ G01F 23/00; G01F 23/284; G01F 23/26; G01F 23/2962; G01F 23/0061; G01F 23/0076; G01F 23/263; G01F 22/00; G01F 23/296; G01F 25/0061; G01F 23/0069; G01F 23/14; G01F 23/18; G01F 23/22; G01F 23/242; G01F 23/268; G01F 23/0007; G01F 23/24; G01F 23/292; G01F 23/2921; G01F 23/2961; G01F 23/04; G01F 23/20; G01F 23/241; G01F 23/265; G01F 23/266; G01F 23/28; G01F 23/2845; G01F 23/2927; G01F 23/30; G01F 23/38; G01F 22/02; G01F 23/0046; G01F 23/162;
(Continued)

(56) References Cited

U.S. PATENT DOCUMENTS 8,491,543 B2 7/2013 Stringham
8,500,673 B2 8/2013 Zanotti et al.
(Continued)

FOREIGN PATENT DOCUMENTS

EP 2350580 9/2012
WO WO 2010/046555 4/2010
(Continued)

OTHER PUBLICATIONS

"Liquid-Level Gauge," *Elektor Electronics.*, 21(235):98-99, Jul. 1, 1995.
(Continued)

*Primary Examiner* — Andre J Allen
(74) *Attorney, Agent, or Firm* — Fish & Richardson P.C.

(57) ABSTRACT

Devices can be used to detect a level of a fluid in a medical fluid reservoir. Methods for controlling the flow rate of a medical pump, and/or the occlusion amount of a medical fluid tube, that are based on the detected level of fluid in the medical reservoir can be used in a clinical setting.

15 Claims, 4 Drawing Sheets

(52) U.S. Cl.
CPC ....... *A61M 1/3667* (2014.02); *A61M 2205/18* (2013.01); *A61M 2205/3317* (2013.01); *A61M 2205/3389* (2013.01)

(58) Field of Classification Search
CPC .. G01F 23/261; G01F 23/288; G01F 23/2928; G01F 23/303; G01F 23/36; G01F 11/00; G01F 11/263; G01F 15/0755; G01F 1/007; G01F 1/24; G01F 23/0015; G01F 23/0023; G01F 23/0053; G01F 23/02; G01F 23/045; G01F 23/16; G01F 23/185; G01F 23/226; G01F 23/243; G01F 23/244; G01F 23/246; G01F 23/248; G01F 23/2885; G01F 23/2965; G01F 23/2966; G01F 23/2968; G01F 23/32; A61M 2205/3379; A61M 2205/3389; A61M 1/16; A61M 2205/14; A61M 2205/15; A61M 2205/18; A61M 2205/3306; A61M 2205/3317; A61M 2205/3331; A61M 2205/3382; A61M 5/1684; A61M 16/1075; A61M 16/109; A61M 16/16; A61M 16/161; A61M 16/162; A61M 1/0001; A61M 1/0023; A61M 1/0025; A61M 1/0031; A61M 1/0088; A61M 1/14; A61M 1/1601; A61M 1/1605; A61M 1/1607; A61M 1/1621; A61M 1/1656; A61M 1/1658; A61M 1/166; A61M 1/1668; A61M 1/1672; A61M 1/1686; A61M 1/28; A61M 1/287; A61M 1/3607; A61M 1/3624; A61M 1/3627; A61M 1/3639; A61M 1/3641; A61M 1/3643; A61M 1/3644; A61M 1/3646; A61M 1/3647; A61M 1/3649; A61M 2202/0413; A61M 2205/121; A61M 2205/123; A61M 2205/33; A61M 2205/332; A61M 2205/3327; A61M 2205/3334; A61M 2205/3337; A61M 2205/3368; A61M 2205/3375; A61M 2205/3386; A61M 2205/3673; A61M 2205/43; A61M 2205/50; A61M 2205/505; A61M 2205/52; A61M 2205/581; A61M 2205/702; A61M 2205/707; A61M 2205/7536; A61M 2209/02; A61M 2230/30; A61M 5/14; A61M 5/1407; A61M 5/1409; A61M 5/1415; A61M 5/142; A61M 5/148
See application file for complete search history.

(56) References Cited

U.S. PATENT DOCUMENTS

| | | | |
|---|---|---|---|
| 2008/0156092 A1 | 7/2008 | Boiarski | |
| 2010/0321478 A1* | 12/2010 | Sliwa | G02B 27/2271 348/51 |
| 2011/0107853 A1* | 5/2011 | Studer | A61M 5/148 73/862.381 |
| 2011/0257578 A1 | 10/2011 | Zanotti et al. | |
| 2016/0334261 A1* | 11/2016 | Wilson, III | G01F 23/24 |

FOREIGN PATENT DOCUMENTS

| | | |
|---|---|---|
| WO | WO 2011/132200 | 10/2011 |
| WO | WO 2012/141756 | 10/2012 |
| WO | WO 2013/003891 | 1/2013 |
| WO | WO 2015/112294 | 7/2015 |

OTHER PUBLICATIONS

Austin, "Evaluation of a "heads-up" display for cardiopulmonary bypass," *J Extra Corpor Technol.*, 32(1):49-53, Mar. 2000.

de Somer et al., "O2 delivery and CO2 production during cardiopulmonary bypass as determinants of acute kidney injury: time for a goal-directed perfusion management?" *Crit Care.*, 15(4):R192, Aug. 10, 2011.

Dijoy et al., "The History of Goal-Directed Therapy and Relevance to Cardiopulmonary Bypass," *J Extra Corpor Technol.*, 47(2):90-94, Jun. 2015.

Goyer, "Why planes are crashing on autopilot," Flying Magazine [online]. Retrieved from the Ineternet: <http://www.flyingmag.com/blogs/going-direct/why-planes-are-crashing-autopilot>, 2 pages, Sep. 4, 2013.

Grist, "CPB FMEA # 31 Human Fatigue Failure," American Society of Extracorporeal Technology [online]. Retrieved from the Internet: <URL: http://www.amsect.org/p/fo/et/thread=1289>, 3 pages, Mar. 25, 2016.

Misgeld, "Automatic Control of the Heart-Lung Machine," Ruhr University Bochum, Germany, [dissertation]. Retrieved from the Internet: <http://www-brs.ub.ruhr-uni-bochum.de/netahtml/HSS/Diss/MisgeldBernoJohannesEngelbert/diss.pdf>, 196 pages, Jul. 27, 2006.

Sorin S5 Brochure, 6 pages, Feb. 1, 2010.

Wilkerson, "Automation of Cardiopulmonary Bypass: An Autopilot for the Heart-lung Machine," Retrieved from the Internet: <URL: http://www.slideshare.net/kwilke859/automation-of-heart-lung-machine>, Oct. 3, 2011, 53 slides.

Wilson, "Autopilot—a New Era in Cardiopulmonary Bypass," California State Perfusion Society's 32nd Annual Fall Tahoe Symposium, Lake Tahoe, Nevada, Sep. 18, 2015, 19 slides.

Wilson, "Pump Automation: A Look at the Future of Perfusion," The 3rd Annual Arizona State Perfusion Society's Wild West Perfusion Conference, Phoenix, AZ, May 7, 2016, 31 slides.

U.S. Appl. No. 15/112,516, filed Jul. 19, 2016, Wilson.

\* cited by examiner

MEDICAL RESERVOIR LEVEL SENSOR

CROSS-REFERENCE TO RELATED APPLICATIONS

This application claims the benefit of U.S. Provisional Application No. 62/336,852, filed May 16, 2016. The disclosure of the prior application is considered part of and is incorporated by reference in the disclosure of this application.

BACKGROUND

1. Technical Field

This document relates to devices for detecting a level of a fluid in a medical fluid reservoir, and methods for controlling the flow rate of a medical pump, and/or the percentage of venous line occlusion of an electronic venous occluder (EVO), based on the detected level of fluid in the medical reservoir.

2. Background Information

Fluid systems commonly include components such as tubing, pumps, reservoirs, heat exchangers, sensors, filters, valves, and the like. Such components can be connected together in a network to define a fluid flow path. Some fluid systems are open systems, meaning that the fluid flows through the network once and then exits the network. Other fluid systems are closed systems, meaning that the fluid recirculates within the network of components. Fluids are caused to flow in the fluid system using fluid pressure differentials. In some cases, a pump is used to create a pressure differential that causes the fluid to flow within the fluid system.

Reservoirs are used as components of fluid systems for various purposes. In some cases, reservoirs are used for accumulation or storage of the fluid. In some cases, the storage of a fluid in a reservoir is used to facilitate a steady outgoing flow of the fluid, despite having an unsteady incoming flow of the fluid. Some reservoirs are completely filled with the fluid, while other reservoirs include an airspace above the level of the fluid in the reservoir.

Fluid systems are often used in a medical context. Some examples of fluid systems used in the medical context include respiratory systems, anesthesia systems, infusion pump systems, blood transfusion circuits, kidney dialysis systems, extracorporeal membrane oxygenation (ECMO) systems, extracorporeal circuits for heart/lung bypass, and the like. Some such medical fluid systems include the use of medical fluid reservoirs. Detection of the level of fluid in the medical fluid reservoir can be useful for various purposes. In some circumstances, the detection of the level of fluid in a medical fluid reservoir can be important for avoiding undesirable consequences that may be risky or inherently detrimental to the health of a patient undergoing treatment using the medical fluid system.

As per Standard 7.9 of the AmSECT 2013 reference: "The percentage of venous line occlusion of the venous occluder shall be monitored continually during CPB." An example of an EVO system is provided in U.S. Pat. No. 8,491,543. Manufacturers of equipment for heart bypass surgery, such as Terumo Cardiovascular Systems and Sorin, market such EVO systems.

SUMMARY

This document provides devices for detecting a level of a fluid in a medical fluid reservoir, and methods for controlling the flow rate of a medical pump and/or the percentage of venous line occlusion of the EVO based on the detected level of fluid in the medical reservoir.

In general, one aspect of this document features a medical fluid reservoir including a reservoir shell defining an interior space that is configured to receive a medical fluid, and a level sensor that is coupled to the reservoir shell. The level sensor includes a plurality of electrode pairs that are electrically uninsulated in relation to the interior space. Individual electrode pairs of the plurality of electrode pairs are disposed at respectively differing elevations in relation to the reservoir shell.

Such a medical fluid reservoir may optionally include one or more of the following features. The level sensor may be adhesively laminated to an interior wall of the reservoir shell. The level sensor may also include a plurality of electrically insulated electrical conductors. Individual ones of the plurality of insulated electrical conductors may be connected to each electrode of the plurality of electrode pairs. The plurality of insulated electrical conductors may be disposed within a wall of the reservoir shell. The plurality of electrode pairs comprises at least three electrode pairs.

In another aspect, this document features medical fluid system including a reservoir shell defining an interior space that is configured to receive a medical fluid; a level sensor that is coupled to the reservoir shell; and a pump system that is configured to pump the medical fluid into or out of the interior space. A speed of the pump system is responsive to a pump speed adjustment input signal. The level sensor includes a plurality of electrode pairs that are electrically uninsulated in relation to the interior space. Individual electrode pairs of the plurality of electrode pairs are disposed at respectively differing elevations in relation to the reservoir shell Such a medical fluid system may optionally include one or more of the following features. The level sensor may be adhesively laminated to an interior wall of the reservoir shell. The level sensor may also include a plurality of electrically insulated electrical conductors. Individual ones of the plurality of insulated electrical conductors may be connected to each electrode of the plurality of electrode pairs. In response to comparative resistances between adjacent electrode pairs, the pump speed adjustment input signal may cause the speed of the pump system to increase or to decrease. The medical fluid system may also include an electronic venous occluder (EVO) that is configured to regulate flow of the medical fluid into or out of the interior space. A percent occlusion of the EVO may be responsive to an EVO controller adjustment input signal.

In another aspect, this document features a method of controlling a level of a medical fluid in a medical fluid reservoir. The method includes: measuring resistances of a plurality of electrode pairs that are electrically uninsulated in relation to an interior space of the medical fluid reservoir; determining differences in resistances between the measured resistances of adjacent electrode pairs of the plurality of electrode pairs; comparing the determined differences in resistances to a threshold value; determining the level of the medical fluid in the medical fluid reservoir based on the comparison of the determined differences in resistances to the threshold value; and in response the determined level, sending a pump speed control signal to a pump speed control system that controls the speed of a pump that propels the medical fluid into or out of the interior space, or sending an electronic venous occluder (EVO) control signal to an EVO control system that controls an amount of occlusion of a tube that allows the medical fluid into or out of the interior space.

Such a method may optionally include one or more of the following features. The medical fluid may be an electrolyte. The medical fluid may include human blood. The plurality of electrode pairs may include at least three electrode pairs. The method may also include repeating the method on a periodic basis.

Particular embodiments of the subject matter described in this document can be implemented to realize one or more of the following advantages. In some medical procedure implementations, a medical reservoir level detection system can be used to automate the control of a pump and/or an EVO system, thereby reducing some of the necessity for on-going direct monitoring of the reservoir by a clinician operator (e.g., perfusionist). Accordingly, the clinician operator may be allowed to attend to other aspects of the medical procedure, thereby enhancing the efficiency of the clinical team. In some embodiments, the use of such automation can allow for the use of a smaller medical reservoir. In some such cases, the medical procedure can therefore be performed with less dilution of the patient's blood. Such improved devices and methods may enhance the overall medical procedure efficacy, improve patient safety, reduce procedure costs, and decrease the stress of operator (e.g., perfusionist).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document provides devices for detecting a level of a fluid in a medical fluid reservoir, methods for controlling the flow rate of a medical pump based on the detected level of fluid in the medical reservoir, and methods for controlling the percent occlusion of an EVO based on the detected level of fluid in the medical reservoir. The devices and methods provided herein are described in the exemplary context of a blood reservoir used for a heart/lung bypass procedure. However, it should be understood that the devices and methods provided herein may be applied in other types of medical fluid systems that include the use of a reservoir.

Figure 1:
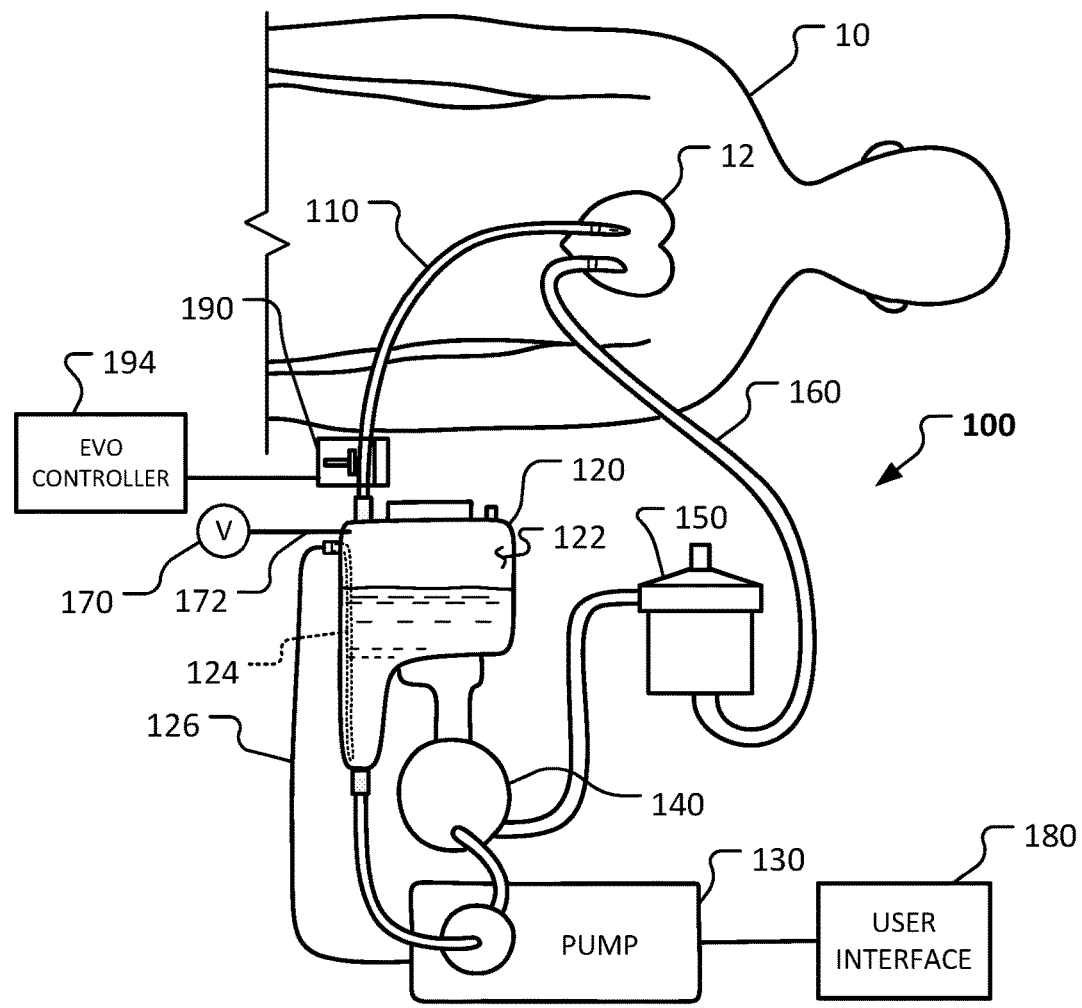
FIG. 1 is a schematic diagram of patient undergoing a medical procedure using a fluid system including a fluid reservoir, in accordance with some embodiments provided herein.

Referring to FIG. 1, a patient 10 can receive a medical treatment while using a medical fluid system 100. In this illustrative example, the patient 10 is undergoing a heart bypass procedure using an extracorporeal blood flow circuit 100. The circuit 100 is connected to the patient 10 at the patient's heart 12 (e.g., the right atrium). Blood from the patient 10 is extracted from the patient 10 at the patient's heart 12; the blood is circulated through the circuit 100; and the blood is then returned to the patient's heart 12 (e.g., at the ascending aorta).

The extracorporeal blood flow circuit 100 includes, at least, a venous tube 110, a blood reservoir 120, a pump 130, an oxygenator/heat exchanger 140, an arterial filter 150, an arterial tube 160, and a user interface 180. The venous tube 110 is in physical contact with the heart 12 and in fluid communication with the venous side of the circulatory system of the patient 10. The venous tube 110 is also in fluid communication with an inlet to the reservoir 120. An outlet from the reservoir 120 is connected by tubing to an inlet of the pump 130. The outlet of the pump 130 is connected to tubing to an inlet of the oxygenator/heat exchanger 140. The outlet of the oxygenator/heat exchanger 140 is connected by tubing to an inlet of the arterial filter 150. In some cases, an arterial filter may be integrated with the oxygenator/heat exchanger 140.

An outlet of the arterial filter 150 is connected to the arterial tube 160. The arterial tube 160 is in physical contact with the heart 12 and in fluid communication with the arterial side of the circulatory system of the patient 10. The user interface 180 can include user input and output devices that are used by the clinician operator (e.g., perfusionist) to properly operate the extracorporeal blood flow circuit 100.

Briefly, the extracorporeal blood flow circuit 100 operates by removing venous blood from the patient 10 via the venous tube 110. Blood from the venous tube 110 is deposited in the reservoir 120. At least some amount of blood is intended to be maintained in the reservoir 120 at all times during the medical procedure. Blood from the reservoir 120 is drawn from the reservoir 120 by the pump 130. The pump 130 can be operated at various speeds which correspond to various flow rates of blood exiting from the reservoir 120. The pressure generated by the pump 130 propels the blood through the oxygenator/heat exchanger 140. In the oxygenator/heat exchanger 140 the venous blood is enriched with oxygen and adjusted to a desired temperature. The oxygen-rich arterial blood exits the oxygenator/heat exchanger 140, travels through the arterial filter 150, and is injected into the patient's heart 12 by the arterial tube 160.

As described above, the venous blood flows (drains) from the heart 12 to the reservoir 120. In some implementations, the venous blood drainage from the heart 12 to the reservoir 120 occurs primarily as a result of gravity. In such gravity drainage implementations the reservoir 120 is positioned at a lower elevation than the heart 12. In result, the blood naturally flows 'downhill' from the heart 12 to the reservoir 120. In some implementations, a vacuum is drawn in the airspace 122 of the reservoir 120 to assist with the drainage from the heart 12 to the reservoir 120. This technique is known as vacuum assisted venous drainage (VAVD). During VAVD procedures, the venous drainage is assisted by placing the reservoir 120 under a negative pressure (vacuum) in relation to the ambient pressure. For example, in some implementations a negative pressure is achieved within the airspace 122 using a vacuum source 170 that is connected to the reservoir 120 via a vacuum line 172. To maintain an effective level of vacuum in the airspace 122 when using VAVD, the reservoir 120 is sealed in an essentially airtight manner.

As described above, the venous blood flows (drains) from the heart 12 to the reservoir 120 through the venous tube 110. In some implementations, an EVO 190 provides precise, controlled and ergonomic operation of venous blood flow during cardiopulmonary bypass. The venous tube 110 passes through the EVO 190. The EVO 190 is adjusted by an EVO controller 194. The EVO 190 regulates the venous blood flow (drainage) from the heart 12 to the reservoir 120 by varying the percent of occlusion placed on the venous tube 110. As the percent venous occlusion increases the internal diameter of the venous tube 110 decreases and venous blood flow (drainage) from the heart 12 to the reservoir 120 decreases. As the percent venous occlusion decreases the internal diameter of the venous tube 110 increases and venous blood flow (drainage) from the heart 12 to the reservoir 120 increases.

The flow of blood through the extracorporeal blood flow circuit 100 is intended to be essentially continuous while the medical procedure is taking place. Within that overall context, an accumulation of blood exists in the reservoir 120 during the procedure. The accumulation of a certain amount of blood in the reservoir 120 is advantageous in some circumstances.

The accumulation of blood within the reservoir 120 serves multiple purposes. For example, in one aspect the accumulation of blood in the reservoir 120 provides a buffer amount to help ensure a continuous flow of oxygenated blood to the patient 10, even in the event that blood flow to the reservoir 120 is interrupted. For example, in some cases a clinician operator of the extracorporeal blood flow circuit 100 may endeavor to maintain an amount of blood in the reservoir that allows for about 12 to 15 seconds of runtime (blood flow to the patient 10) in the event that no more blood is added into the reservoir 120. In another example aspect, the reservoir 120 allows the venous blood to deaerate. The deaeration of the venous blood takes place by allowing air bubbles in the blood to escape the blood and flow (rise) into the air. For at least that reason, an airspace 122 is maintained in the reservoir 120.

To assist the clinician operator (e.g., perfusionist) of the extracorporeal blood flow circuit 100 to maintain a desired amount of accumulated blood in the reservoir 120, a reservoir level sensor 124 in accordance with the present disclosure can be provided. The level sensor 124 is responsive to the level of blood in the reservoir 120. That is, the level sensor 124 provides an indication of the level of blood in the reservoir 120. The level sensor 124 can be in electrical communication with the control system for the pump 130 and/or the user interface 180 via an electrical cable 126.

The indication of the level of blood in the reservoir 120 provided by the level sensor 124 can be used to control the speed of the pump 130 in some embodiments. For example, if the level sensor 124 indicates that the level of blood in the reservoir 120 is above a set point (or set range), the indication can be used to increase the flow rate of the pump 130. Such an increased flow rate will tend to cause the level of blood in the reservoir 120 to be reduced. Conversely, if the level sensor 124 indicates that the level of blood in the reservoir 120 is below a set point (or set range), the indication can be used to decrease the flow rate of the pump 130. Such a decreased flow rate will tend to cause the level of blood in the reservoir 120 to be increased.

The indication of the level of blood in the reservoir 120 provided by the level sensor 124 can be used to control the percent venous occlusion of the EVO 190 in some embodiments. For example, if the level sensor 124 indicates that the level of blood in the reservoir 120 is above a set point (or set range), the indication can be used to increase the percent venous occlusion of the EVO 190 thereby decreasing venous blood drainage to the reservoir 120. Such a decreased venous blood flow drainage rate will tend to cause the level of blood in the reservoir 120 to be reduced. Conversely, if the level sensor 124 indicates that the level of blood in the reservoir 120 is below a set point (or set range), the indication can be used to decrease the percent venous occlusion of the EVO 190 thereby increasing venous blood drainage to the reservoir 120. Such an increased venous blood flow drainage rate will tend to cause the level of blood in the reservoir 120 to be increased.

In some embodiments, the indication of the level of blood in the reservoir 120 provided by the level sensor 124 can be used to trigger alerts or alarms for receipt by the clinician operator. Such alerts or alarms can be provided via the user interface 180. Such alerts or alarms can be provided in lieu of, or in addition to, changing the speed of the pump 130 and/or changing the occlusion of the EVO 190.

In some embodiments, system parameters can be established whereby the automated responsiveness of the pump 130 and/or EVO 190, as described above, are further defined and/or controlled. For example, in some embodiments the aggressiveness (e.g., the pump gain/acceleration) of the pump speed changes and/or EVO occlusion changes can be selectively programmed into the system parameters. In another example, maximum or minimum pump speeds and/or EVO occlusion can be selectively programmed into the system parameters. In a further example, alarm limits can be selectively programmed into the system parameters. It is also envisioned that other such system parameters can also be selectively programmed into the system parameters.

Figure 3:
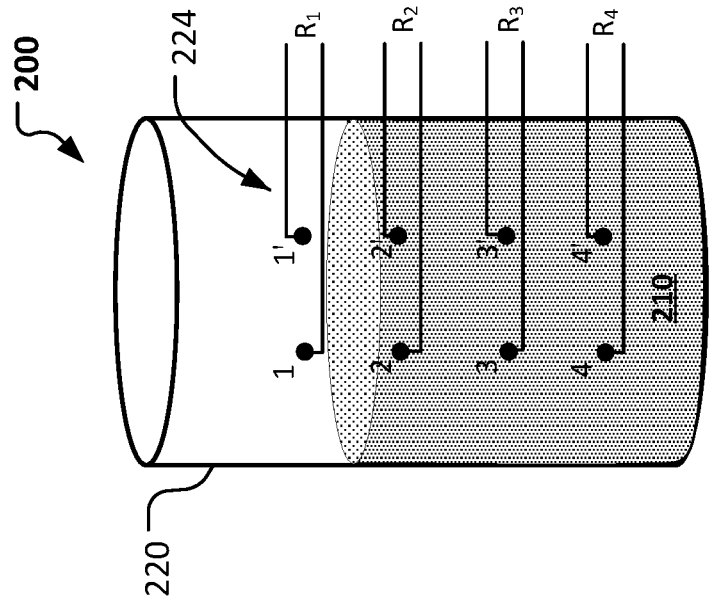
FIG. 3 is another schematic diagram of the example reservoir level sensor system of FIG. 2.
Figure 2:
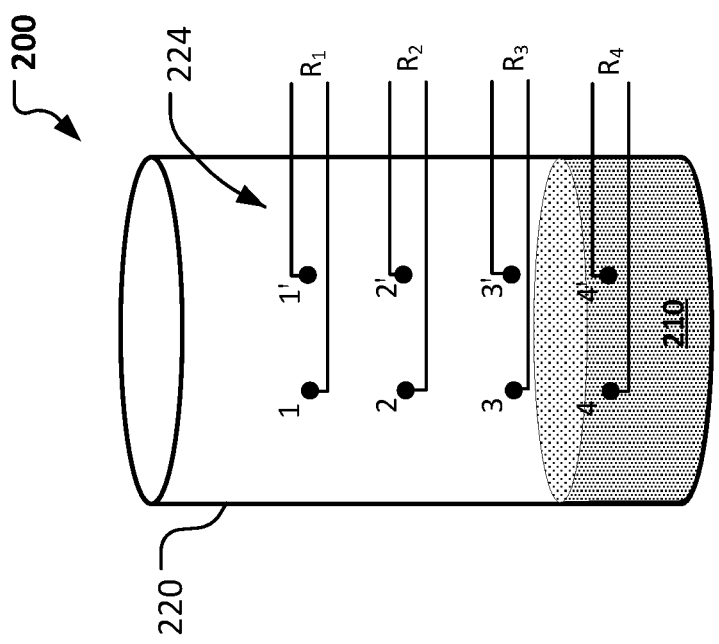
FIG. 2 is a schematic diagram of an example reservoir level sensor system in accordance with some embodiments.

Referring now to FIGS. 2 and 3, a medical fluid reservoir 200 can include a reservoir shell 220 and a level sensor 224. Level sensor 224 can be used to detect a level of a fluid 210 by measuring the resistance of a conductive fluid (e.g., an electrolytic liquid such as, but not limited to, blood, saline, etc.) in reservoir shell 220.

In the depicted embodiment, level sensor 224 includes a plurality of electrode pairs (i.e., electrode pair 1-1', electrode pair 2-2', electrode pair 3-3', and electrode pair 4-4'). While in the depicted embodiment four electrode pairs 1-1', 2-2', 3-3', and 4-4' are included, in some embodiments two, three, four, five, six, seven, eight, nine, ten, or more than ten electrode pairs are included on reservoir shell 220.

In order to differentiate the level of fluid 210 using electrode pairs 1-1', 2-2', 3-3', and 4-4', each electrode pair of the plurality of electrode pairs 1-1', 2-2', 3-3', and 4-4' can be positioned at a different elevation on reservoir shell 220. Accordingly, as described further below, by measuring a resistance level of each of the electrode pairs 1-1', 2-2', 3-3', and 4-4', and then comparing the resistance levels, the level of fluid 210 in reservoir shell 220 can be determined.

While the electrodes of an electrode pair 1-1', 2-2', 3-3', and/or 4-4' are out of contact with fluid 210, there is essentially an infinite resistance between the electrodes of the electrode pair 1-1', 2-2', 3-3', and 4-4'. For example, in the example of FIG. 2, a resistance $R_1$ (the resistance between electrodes 1 and 1') is essentially infinite (or a very high number corresponding to the resistance of the gas above fluid 210) because fluid 210 is not in contact with electrodes 1 and 1'. Conversely, in the example of FIG. 2, a resistance $R_4$ (the resistance between electrodes 4 and 4') is much lower (e.g., on the order of ohms, kilohms, or megohms in some cases) because conductive fluid 210 is in contact with electrodes 4 and 4'. It follows that resistance $R_1$ between electrodes 1 and 1', $R_2$ between electrodes 2 and 2', and a resistance $R_3$ between electrodes 3 and 3' are each essentially infinite because fluid 210 is not in contact with electrodes 1 and 1', 2 and 2' or with electrodes 3 and 3'.

By detecting resistances $R_1$, $R_2$, $R_3$, and $R_4$ the level of fluid 210 in reservoir shell 220 can be ascertained. For instance, in the example of FIG. 2, knowing that resistances $R_1$, $R_2$, and $R_3$ are infinite, while resistance $R_4$ is much lower, it can be concluded that the level of fluid 210 is between electrode pair 3-3' and electrode pair 4-4'. In the example of FIG. 3, knowing that resistance $R_1$ is infinite, while resistances $R_2$, $R_3$, and $R_4$ are much lower, it can be concluded that the level of fluid 210 is between electrode pair 1-1' and electrode pair 2-2'. It follows that a substantial change in resistance (e.g., $R_1$ compared to $R_2$, $R_2$ compared to $R_3$, or $R_3$ compared to $R_4$) between adjacent electrode pairs 1-1', 2-2', 3-3', and/or 4-4' indicates that the level of fluid 210 is between the adjacent electrode pairs 1-1', 2-2', 3-3', and/or 4-4' exhibiting the substantial change in resistance therebetween.

Figure 4:
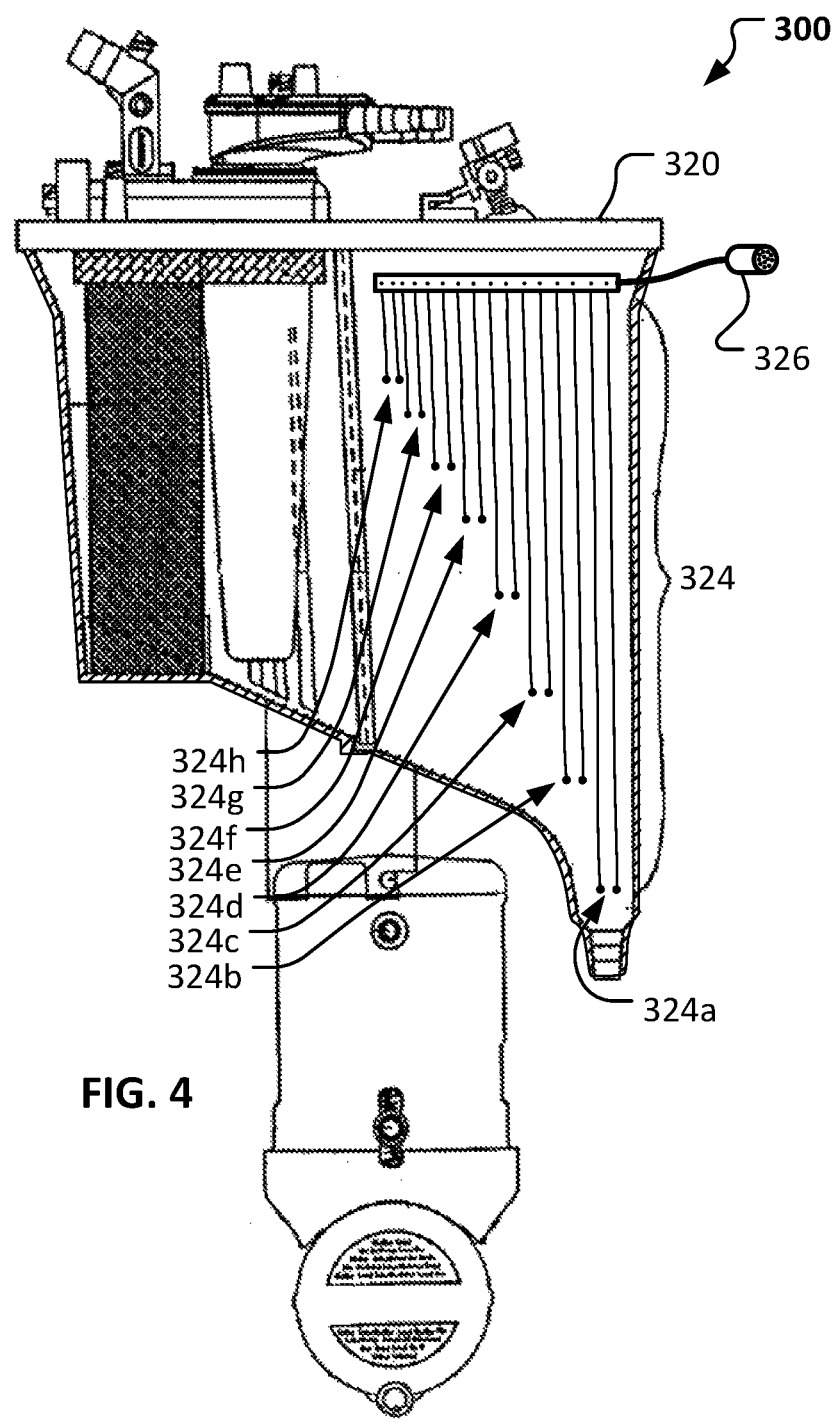
FIG. 4 is a cutaway view of another example level sensor system mounted in a medical fluid reservoir, in accordance with some embodiments provided herein.

Referring now to FIG. 4, another example level sensor system 324 can be configured at least partially within the interior of a reservoir 320. The reservoir 320 is shown in a partial cross-sectional view to provide visualization of the interior of the reservoir 320. In this configuration of level sensor system 324, electrode pairs of level sensor system 324 can be in direct contact with the liquid contents of the reservoir 320 (such as blood, saline, or other medical fluids) while the electrical conductors connected to the electrode pairs are insulated from liquid contact.

The level sensor system 324 includes two or more individual electrode pairs (e.g., as described above in reference to level sensor 224). In the depicted embodiment, the level sensor system 324 includes eight electrode pairs 324a, 324b, 324c, 324d, 324e, 324f, 324g, and 324h. While the depicted embodiment includes eight level sensors, in some embodiments two, three, four, five, six, seven, nine, ten, or more than ten electrode pairs are included in the level sensor system 324.

Each individual electrode of electrode pairs 324a, 324b, 324c, 324d, 324e, 324f, 324g, and 324h is connected to an insulated conductive wire (or trace) that is electrically coupled to a pin at a multi-pin connector 326. Multi-pin connector 326 can be electrically coupled to a controller or interface of a medical fluid circuit (such as the extracorporeal blood flow circuit 100 of FIG. 1). Accordingly, level sensor system 324 can be used as feedback for controlling a level of fluid in reservoir 320 (as described further below).

Each electrode pair 324a, 324b, 324c, 324d, 324e, 324f, 324g, and 324h is positioned at a differing depth level within the reservoir 320. In other words, the locations of electrode pairs 324a, 324b, 324c, 324d, 324e, 324f, 324g, and 324h provide a graduated level sensor system 324 for indicating the level of a liquid within the reservoir 320.

As described above in reference to level sensor 224, the comparative resistances of adjacent electrode pairs 324a, 324b, 324c, 324d, 324e, 324f, 324g, and 324h can be used to detect a level of fluid within the reservoir 320. An abrupt increase (or decrease) in the resistance of adjacent electrode pairs (e.g., 324a compared to 324b, 324b compared to 324c, 324c compared to 324d, 324d compared to 324e, 324e compared to 324f, 324f compared to 324g, or 324g compared to 324h) indicates that the level of fluid within the reservoir 320 is between those adjacent electrode pairs.

If the resistances of all electrode pairs 324a, 324b, 324c, 324d, 324e, 324f, 324g, and 324h are essentially infinite, it can be ascertained that the level of fluid within the reservoir 320 is below the position of electrode pair 324a. In such a scenario, a speed of a pump that draws the liquid from the reservoir 320 can be slowed or stopped so as to increase the level of the liquid, for example and/or the occlusion of an EVO that allows the liquid into the reservoir 320 can be decreased so as to increase the level of the liquid, for example.

Conversely, if the resistances of all electrode pairs 324a, 324b, 324c, 324d, 324e, 324f, 324g, and 324h are indicative of contact of the electrode pairs 324a, 324b, 324c, 324d, 324e, 324f, 324g, and 324h with the fluid, it can be ascertained that the level of fluid within the reservoir 320 is above the position of electrode pair 324h. In such a scenario, a speed of a pump that draws the liquid from the reservoir 320 can be sped up so as to lower the level of the liquid, for example and/or the occlusion of an EVO that allows the liquid into the reservoir 320 can be increased so as to lower the level of the liquid, for example.

In some embodiments, level sensor 324 is laminated on an interior wall of reservoir 320. That is, in some embodiments level sensor 324 is attached, adhered, mounted, etc., to an interior wall of reservoir 320. For example, in some embodiments level sensor 324 can comprise a flexible substrate with an adhesive on the side adjacent to the interior wall of reservoir 320. Alternatively, in some embodiments level sensor 324 is molded within the interior wall of reservoir 320 (except that electrode pairs 324a, 324b, 324c, 324d, 324e, 324f, 324g, and 324h are exposed to the interior of reservoir 320 such that they can be in contact with fluid contained in the reservoir 320). Further, in some embodiments level sensor 324 is attached, adhered, mounted, etc., to an exterior wall of reservoir 320 (except that electrode pairs 324a, 324b, 324c, 324d, 324e, 324f, 324g, and 324h are exposed to the interior of reservoir 320 such that they can be in contact with fluid contained in the reservoir 320).

In some embodiments, a wireless interface (not shown) is included that can wirelessly transmit the resistance of electrode pairs 324a, 324b, 324c, 324d, 324e, 324f, 324g, and 324h to a receiver of a controller or interface of a medical fluid circuit (such as the extracorporeal blood flow circuit 100 of FIG. 1).

Figure 5:
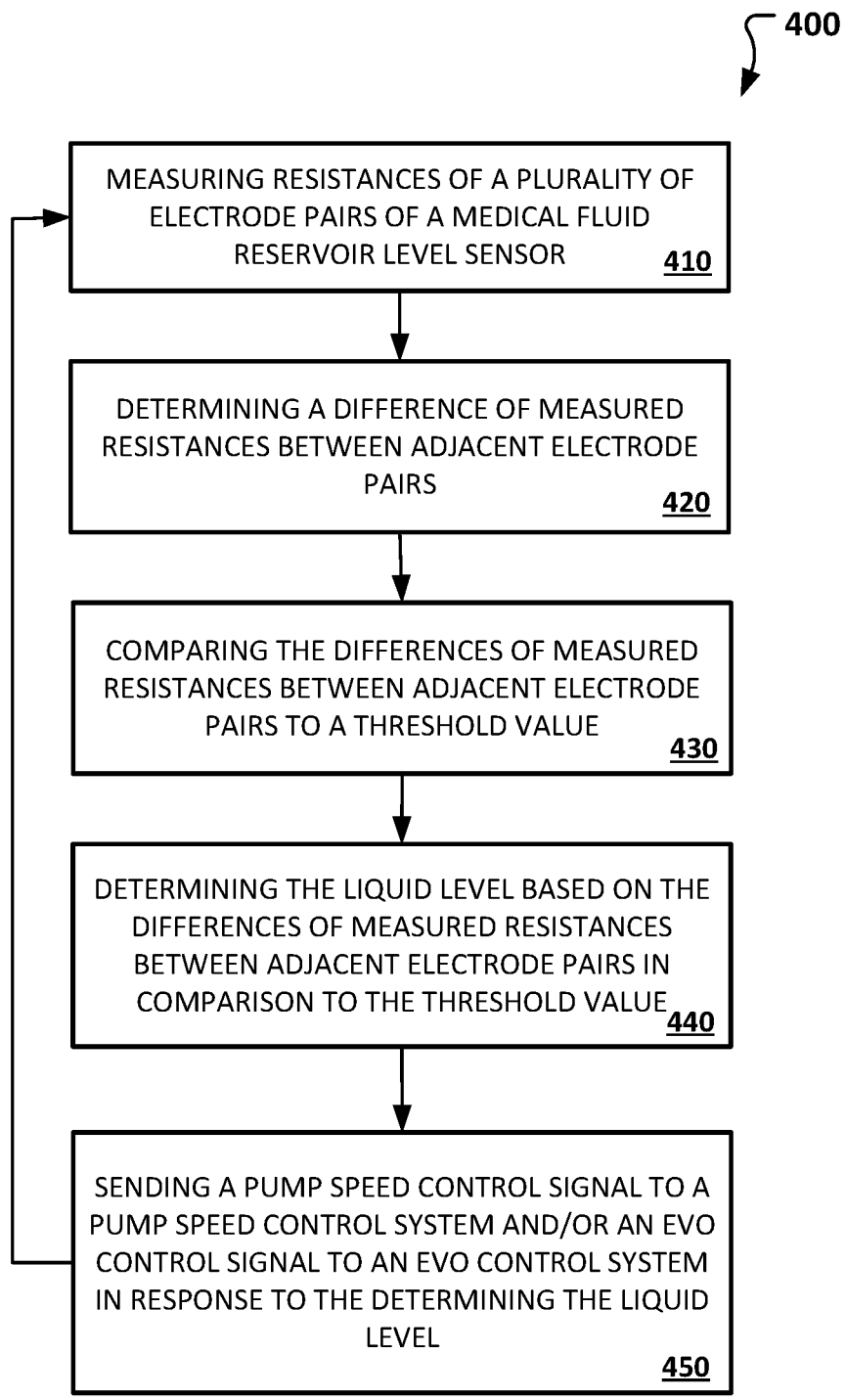
FIG. 5 is flowchart of a method for controlling the speed of a pump and/or the percent occlusion by an EVO system in response to a level sensor signal, in accordance with some embodiments provided herein.

Referring now to FIG. 5, an example method 400 for using a medical fluid reservoir level sensor to adjust the speed of a pump and/or occlusion of an EVO is provided. For example, the method 400 can be used in the context of a medical fluid circuit such as the extracorporeal blood flow circuit 100 of FIG. 1 that includes reservoir 120, level sensor 124, pump 130, and EVO 190. In some cases, a controller of a medical fluid circuit such as the extracorporeal blood flow circuit 100 can perform method 400. Method 400 can be repeated on any suitable periodic basis such as about every second, about every five seconds, about every 10 seconds, and the like.

At operation 410, the resistances of a plurality of electrode pairs of a medical fluid reservoir level sensor are received/measured. Individual electrode pairs of the plurality of electrode pairs are at differing locations (e.g., elevations) in relation to the reservoir.

For example, in the context of level sensor 324 described above, the resistances of electrode pairs 324a, 324b, 324c, 324*d*, 324*e*, 324*f*, 324*g*, and 324*h* can be received/measured. When liquid is not in contact with a particular electrode pair, the resistance between the electrodes of the electrode pair will be essentially infinite. But, when liquid is in contact with a particular electrode pair, the resistance between the electrodes of the electrode pair will be measurable (e.g., typically on the order of ohms, kilohms, or megohms).

If the resistances of all electrode pairs 324*a*, 324*b*, 324*c*, 324*d*, 324*e*, 324*f*, 324*g*, and 324*h* are infinite, the controller executing method 400 can determine that the liquid level is below the lowest electrode pair, and can proceed next to step 450. If the resistances of all electrode pairs 324*a*, 324*b*, 324*c*, 324*d*, 324*e*, 324*f*, 324*g*, and 324*h* are measurable, the controller executing method 400 can determine that the liquid level is above the highest electrode pair, and can proceed next to step 450.

At operation 420, the measured resistances of adjacent electrode pairs of the level sensor from operation 410 are compared to each other to determine a resistance difference. The differences between the resistances of the adjacent electrode pairs can be used to identify a level of liquid in the reservoir as described herein.

At operation 430, the differences between the resistances of adjacent electrode pairs (as determined in operation 420) are compared to a threshold value.

At operation 440, the liquid level is determined based on the comparison of the resistance differences between adjacent electrode pairs and the threshold value (as performed in operation 430). For example, if the resistance difference between two particular adjacent electrode pairs is below the threshold value, the liquid level is determined to not be between the two particular adjacent electrodes. However, if the resistance difference between two other particular adjacent electrode pairs is above the threshold value, the liquid level is determined to be between the two other particular adjacent electrodes.

At operation 450, a pump speed control signal or an EVO control signal is sent by the controller of the fluid circuit in response to determining the liquid level in operation 440. If the liquid level is determined to be above a target range, a pump speed signal to increase the speed of the pump is sent to the pump speed control system (to drain the reservoir at a faster pace) and/or an EVO occlusion adjustment signal to increase the percent occlusion may be sent to the EVO control system (to slow the flow of liquid entering the reservoir). If the liquid level is determined to be below a target range, a pump speed signal to decrease the speed of the pump is sent to the pump speed control system (to drain the reservoir at a slower pace) and/or an EVO occlusion adjustment signal to decrease the percent occlusion may be sent to the EVO control system (to quicken the flow of liquid entering the reservoir).

After operation 450, the method 400 can be repeated by reverting to operation 410.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying FIG.s do not necessarily require the particular order shown, or sequential order, to achieve desirable results. In certain implementations, multitasking and parallel processing may be advantageous.

What is claimed is:

1. A medical fluid reservoir comprising:
   a reservoir shell defining an interior space that is configured to receive a medical fluid; and
   a level sensor that is coupled to the reservoir shell, the level sensor comprising a plurality of electrode pairs that are electrically uninsulated in relation to the interior space, the plurality of electrode pairs including a first electrode pair and a second electrode pair, and wherein the first electrode pair is disposed at a different elevation in relation to the reservoir shell than the second electrode pair.

2. The medical fluid reservoir of claim 1, wherein the level sensor is adhesively laminated to an interior wall of the reservoir shell.

3. The medical fluid reservoir of claim 1, wherein the level sensor further comprises a plurality of electrically insulated electrical conductors, wherein individual ones of the plurality of insulated electrical conductors are connected to each electrode of the plurality of electrode pairs.

4. The medical fluid reservoir of claim 3, wherein the plurality of insulated electrical conductors are disposed within a wall of the reservoir shell.

5. The medical fluid reservoir of claim 1, wherein the plurality of electrode pairs comprises at least three electrode pairs.

6. A medical fluid system comprising:
   a reservoir shell defining an interior space that is configured to receive a medical fluid;
   a level sensor that is coupled to the reservoir shell, the level sensor comprising a plurality of electrode pairs that are electrically uninsulated in relation to the interior space, the plurality of electrode pairs including a first electrode pair and a second electrode pair, and wherein the first electrode pair is disposed at a different elevation in relation to the reservoir shell than the second electrode pair; and
   a pump system that is configured to pump the medical fluid into or out of the interior space, wherein a speed of the pump system is responsive to a pump speed adjustment input signal.

7. The medical fluid system of claim 6, wherein the level sensor is adhesively laminated to an interior wall of the reservoir shell.

8. The medical fluid system of claim 6, wherein the level sensor further comprises a plurality of electrically insulated electrical conductors, wherein individual ones of the plurality of insulated electrical conductors are connected to each electrode of the plurality of electrode pairs.

9. The medical fluid system of claim 6, wherein, in response to comparative resistances between adjacent electrode pairs, the pump speed adjustment input signal causes the speed of the pump system to increase or to decrease.

10. The medical fluid system of claim 6, further comprising an electronic venous occluder (EVO) that is configured to regulate flow of the medical fluid into or out of the interior space, wherein a percent occlusion of the EVO is responsive to an EVO controller adjustment input signal.

11. A method of controlling a level of a medical fluid in a medical fluid reservoir, the method comprising:
    measuring resistances of a plurality of electrode pairs that are electrically uninsulated in relation to an interior space of the medical fluid reservoir, the plurality of electrode pairs including a first electrode pair and a second electrode pair, wherein the first electrode pair is disposed at a different elevation in relation to the reservoir shell than the second electrode pair;
    determining differences in resistances between the measured resistances of the first electrode pair and the second electrode pair;
    comparing the determined differences in resistances to a threshold value;
    determining the level of the medical fluid in the medical fluid reservoir based on the comparison of the determined differences in resistances to the threshold value; and
    controlling the level of the medical fluid in the medical fluid reservoir by:
        (i) sending a pump speed control signal to a pump speed control system that controls the speed of a pump that propels the medical fluid into or out of the interior space, wherein the pump speed control signal is established based on the determined level of the medical fluid in the medical fluid reservoir; or
        (ii) sending an electronic venous occluder (EVO) control signal to an EVO control system that controls an amount of occlusion of a tube that allows the medical fluid into or out of the interior space, wherein the EVO control signal is established based on the determined level of the medical fluid in the medical fluid reservoir.

12. The method of claim 11, wherein the medical fluid is an electrolyte.

13. The method of claim 12, wherein the medical fluid comprises human blood.

14. The method of claim 11, wherein the plurality of electrode pairs comprises at least three electrode pairs.

15. The method of claim 11, further comprising repeating the method on a periodic basis.

* * * * *